United States Patent
Yan et al.

(10) Patent No.: US 11,925,213 B2
(45) Date of Patent: Mar. 12, 2024

(54) OUTPUT CONTROL CIRCUIT

(71) Applicant: SHENZHEN FIRST UNION TECHNOLOGY CO., LTD., Shenzhen (CN)

(72) Inventors: Huiyong Yan, Shenzhen (CN); Zhongli Xu, Shenzhen (CN); Yonghai Li, Shenzhen (CN)

(73) Assignee: SHENZHEN FIRST UNION TECHNOLOGY CO., LTD., Shenzhen (CN)

( * ) Notice: Subject to any disclaimer, the term of this patent is extended or adjusted under 35 U.S.C. 154(b) by 530 days.

(21) Appl. No.: 17/280,817

(22) PCT Filed: Sep. 27, 2019

(86) PCT No.: PCT/CN2019/108554
§ 371 (c)(1),
(2) Date: Mar. 26, 2021

(87) PCT Pub. No.: WO2020/063869
PCT Pub. Date: Apr. 2, 2020

(65) Prior Publication Data
US 2021/0401058 A1   Dec. 30, 2021

(30) Foreign Application Priority Data

Sep. 29, 2018   (CN) .......................... 201811152024.3

(51) Int. Cl.
*A24F 40/50*   (2020.01)
*A24F 40/90*   (2020.01)
(Continued)

(52) U.S. Cl.
CPC .............. *A24F 40/50* (2020.01); *A24F 40/90* (2020.01); *A61M 11/042* (2014.02);
(Continued)

(58) Field of Classification Search
CPC ....... A61M 11/042; A24F 40/50; A24F 40/90; H02J 7/0029; H02J 7/0042; H02M 3/155
(Continued)

(56) References Cited

U.S. PATENT DOCUMENTS

2018/0035714 A1*   2/2018   Sur .......................... H02M 3/04
2018/0132530 A1*   5/2018   Rogers .................... A24F 40/53
(Continued)

FOREIGN PATENT DOCUMENTS

CN   104055224 A   *   9/2014   .......... A24F 47/008
CN   102790375 B   *   4/2015
(Continued)

*Primary Examiner* — Peter G Leigh
(74) *Attorney, Agent, or Firm* — Cheng-Ju Chiang

(57) ABSTRACT

An output control circuit is applied in an electronic cigarette including a battery assembly and an atomizer. The output control circuit includes a controller, a first switching circuit, a driving circuit and a second switching circuit. The controller is for controlling switching-on or switching-off of the first switching circuit, and providing PWM signals to the driving circuit. The first switching circuit is respectively electrically connected with the battery assembly, the controller and the atomizer. The driving circuit is used for driving to switch on or switch off the second switching circuit according to the PWM signals. The second switching circuit is respectively electrically connected with the battery assembly, the driving circuit and the atomizer. The first switching circuit, the atomizer and the second switching circuit are electrically connected in series. The atomizer is switched on when the first switching circuit and the second switching circuit are switched on simultaneously.

17 Claims, 3 Drawing Sheets

(51) Int. Cl.
    *A61M 11/04*     (2006.01)
    *H02J 7/00*      (2006.01)
    *H02M 3/155*     (2006.01)

(52) U.S. Cl.
    CPC .......... *H02J 7/0029* (2013.01); *H02J 7/0042* (2013.01); *H02M 3/155* (2013.01)

(58) Field of Classification Search
    USPC ......................................................... 131/329
    See application file for complete search history.

(56) References Cited

U.S. PATENT DOCUMENTS

2019/0246698 A1* 8/2019 Nakano .................. A24F 40/57
2019/0246701 A1* 8/2019 Nakano ................ H05B 1/0225

FOREIGN PATENT DOCUMENTS

| | | | | |
|---|---|---|---|---|
| CN | 204759079 U | * | 11/2015 | |
| CN | 105686087 A | | 6/2016 | |
| CN | 206714086 U | | 12/2017 | |
| CN | 207319008 U | | 5/2018 | |
| CN | 109497615 A | | 3/2019 | |
| CN | 110083194 A | * | 8/2019 | |
| GB | 2531415 A | | 4/2016 | |
| KR | 10-1570876 B1 | | 11/2015 | |
| WO | WO-2018092036 A1 | * | 5/2018 | ............. A24F 40/10 |
| WO | WO-2018198152 A1 | * | 11/2018 | ........... A24B 15/167 |
| WO | WO-2018198153 A1 | * | 11/2018 | ........... A24B 15/167 |
| WO | WO-2018198154 A1 | * | 11/2018 | ........... A24B 15/167 |

* cited by examiner

OUTPUT CONTROL CIRCUIT

CROSS REFERENCE TO RELATED APPLICATIONS

The present application is a 35 U.S.C. § 371 National Phase conversion of International (PCT) Patent Application No. PCT/CN2019/108554, filed on Sep. 27, 2019, which claims priority of Chinese Patent Application No. 201811152024.3, filed on Sep. 29, 2018 in China National Intellectual Property Administration, the entire disclosure of which is incorporated by reference herein. The PCT International Patent Application was filed and published in Chinese.

BACKGROUND OF THE INVENTION

1. Field of the Invention

The present invention relates to a technical field of electronic cigarettes, particularly relates to an output control circuit thereof.

2. The Related Arts

Electronic cigarettes are a kind of relatively common simulative electronic-cigarette electronic products. The electronic cigarettes are mainly used for quitting cigarettes and substituting cigarettes. Main structures of an electronic cigarette include a battery rod and an atomizer. When a smoke inhaling action from smokers is detected, the battery rod supplies power to the atomizer to turn on the atomizer. When the atomizer is turned on, heating wires of the atomizer heat up, and tobacco liquid is heated and atomized to form an aerosol that simulates cigarette smoke. As a result, smokers have a similar experience for smoking electronic cigarettes to experience for smoking cigarettes.

In the process of realizing the present application, the named inventor found that the related technology as described above has the following problem. Currently, the existing electronic cigarette controls power output of the atomizer through a single switch circuit. When smoking, a controller controls to turn on the single switch circuit, and further turn on the atomizer. When smoking is finished, the controller controls to turn off the single switch circuit, and the atomizer is therefore turned off. Such output control circuit of the above mentioned electronic cigarette has a simple structure and a better cost advantage. However, when the controller fails or is in an abnormal state, or when the single switch circuit fails, the atomizer of the electronic cigarette is hence led to turn on and continue to output power. As a result, safety risks such as fire, etc., may be caused.

SUMMARY OF THE INVENTION

In order to solve the aforementioned technical problem, an output control circuit is provided in accordance with a preferred embodiment of the present invention, and reliability and safety of products related to the output control circuit are therefore enhanced.

In order to solve the aforementioned technical problem, an output control circuit applied in an electronic cigarette is provided in accordance with a preferred embodiment of the present invention. The electronic cigarette includes a battery assembly and an atomizer. The output control circuit includes a controller, a first switching circuit, a driving circuit and a second switching circuit. The controller is used to control switching-on or switching-off of the first switching circuit, and to provide pulse-width modulation (PWM) signals to the driving circuit.

The first switching circuit is respectively electrically connected with the battery assembly, the controller and the atomizer.

The driving circuit is electrically connected with the controller. The driving circuit is used for driving to switch on or switch off the second switching circuit according to the PWM signals.

The second switching circuit is respectively electrically connected with the battery assembly, the driving circuit and the atomizer.

The controller is electrically connected with the battery assembly.

The first switching circuit, the atomizer and the second switching circuit are electrically connected in series. The atomizer is switched on when the first switching circuit and the second switching circuit are switched on simultaneously.

Alternatively, the driving circuit includes a trigger circuit, a monostable circuit and a pulse width modulation (PWM) circuit.

The trigger circuit is respectively electrically connected with the battery assembly, the controller, the monostable circuit and the PWM circuit. The trigger circuit is used for triggering the controller to decide whether or not the monostable circuit is provided with PWM signals.

The monostable circuit is respectively electrically connected with the battery assembly, the controller, the second switching circuit and the PWM circuit. The monostable circuit includes an input and an output. The input of the monostable circuit is used to receive PWM signals, and the output of the monostable circuit is used to output high voltage level signals or low voltage level signals in order to control switching on or switching off of the second switching circuit based on the received PWM signals.

The PWM circuit is further electrically connected with the battery assembly. The PWM circuit is used to regulate pulse widths of the high voltage level signals or low voltage level signals.

Alternatively, the trigger circuit includes a first resistor and a switch.

A first end of the first resistor is electrically connected with the controller, and a second end of the first resistor is electrically connected with the monostable circuit.

A first end of the switch is electrically connected with the first end of the first resistor, and a second end of the switch is electrically connected with ground.

Alternatively, the PWM circuit includes a second resistor and a first capacitor.

A first end of the second resistor is respectively electrically connected with the battery assembly and the second end of the first resistor. A second end of the second resistor is respectively electrically connected with a first end of the first capacitor and the monostable circuit.

A second end of the first capacitor is electrically connected with ground.

Alternatively, the first switching circuit includes a second capacitor, a third resistor, a fourth resistor and a first metal oxide semiconductor field effect transistor (MOS) tube.

A first end of the second capacitor is electrically connected with the battery assembly, and a second end of the second capacitor is electrically connected with ground.

A first end of the third resistor is respectively electrically connected with the first end of the second capacitor and a source electrode of the first MOS tube. A second end of the third resistor is respectively electrically connected with the controller and a first end of the fourth resistor.

A second end of the fourth resistor is electrically connected with a gate electrode of the first MOS tube.

A drain electrode of the first MOS tube is electrically connected with a positive electrode of the atomizer.

Alternatively, the second switching circuit includes a second MOS tube. A gate electrode of the second MOS tube is electrically connected with an output of a monostable circuit of the driving circuit. A source electrode of the second MOS tube is electrically connected with ground. A drain electrode of the second MOS tube is electrically connected with a negative electrode of the atomizer.

Alternatively, the output control circuit further includes a current-limiting circuit. The current-limiting circuit is parallel electrically connected between the positive electrode of the atomizer and the negative electrode of the atomizer.

The current-limiting circuit includes a fifth resistor. The fifth resistor is used for restricting a quantity of electrical currents flowing into the atomizer.

Alternatively, the battery assembly includes the following.

A charging circuit is included.

A protective circuit is included. The protective circuit is electrically connected with the charging circuit.

A lithium battery is included. The lithium battery is electrically connected with the protective circuit.

A voltage stabilizing buck circuit is included. The voltage stabilizing buck circuit is respectively electrically connected with the lithium battery, the controller and the driving circuit.

Alternatively, the output control circuit further includes a prompt circuit. The prompt circuit is respectively electrically connected with the charging circuit and the controller.

The prompt circuit includes a sixth resistor and a light-emitting diode (LED) tube. A first end of the sixth resistor is electrically connected with the charging circuit, and a second end of the sixth resistor is electrically connected with a positive electrode of the LED tube. A negative electrode of the LED tube is electrically connected with the controller.

Alternatively, the atomizer includes a heating assembly and a temperature detecting circuit connected with the heating assembly. The temperature detecting circuit is electrically connected with the controller, and is used to detect temperature values of the heating assembly and to transmit the temperature values to the controller.

Beneficial advantages of the present invention include the following. In comparison with existing technology, the output control circuit is provided in accordance with a preferred embodiment of the present invention. Switching on of the atomizer is simultaneously controlled by the first switching circuit and the second switching circuit. Safety risk such as fire incidents is accordingly avoided when the atomizer of the electronic cigarette continuously outputs power due to the controller being out of order, either one of the first and second switching circuits being out of order, or the controller being in the malfunctioned status. Reliability and safety of products related to the electronic cigarette are therefore enhanced.

BRIEF DESCRIPTION OF THE DRAWINGS

One or more embodiments in accordance with the present invention are illustratively exemplified for explanation through figures shown in the corresponding attached drawings. These exemplified descriptions do not constitute any limitation on the embodiments. The elements with the same reference numerals in the attached drawings are denoted as similar elements. Unless otherwise stated, the figures in the attached drawings do not constitute any scale limitation.

DETAILED DESCRIPTION OF PREFERRED EMBODIMENT

In order to facilitate best understanding of the present invention, the present invention will be illustrated in more detail below in conjunction with the attached drawings and preferred embodiments. It should be noted that when an element is expressed as "being fixed to" another element, this element may be directly on the another element, or there may be one or more intervening elements between this element and the another element. When an element is expressed as "being connected to" another element, this element can be directly connected to the another element, or there may be one or more intervening elements between this element and the another element. In addition, terminology such as "first", "second", etc., is only used for descriptive purposes, and cannot be understood as indicating or implying relative importance.

Unless otherwise defined, any technical and scientific terminology used in this specification has the same meaning as commonly understood by those skilled in the technical field of the present invention. Terminology used in this specification of the present invention is only for a purpose of describing specific embodiments, and is not used to limit the present invention. Terminology such as "and/or" used in this specification includes any and all combinations of one or more related listed items.

In addition, technical features involved in different embodiments of the present invention described below can be mutually combined as long as they do not conflict with one another.

Figure 1:
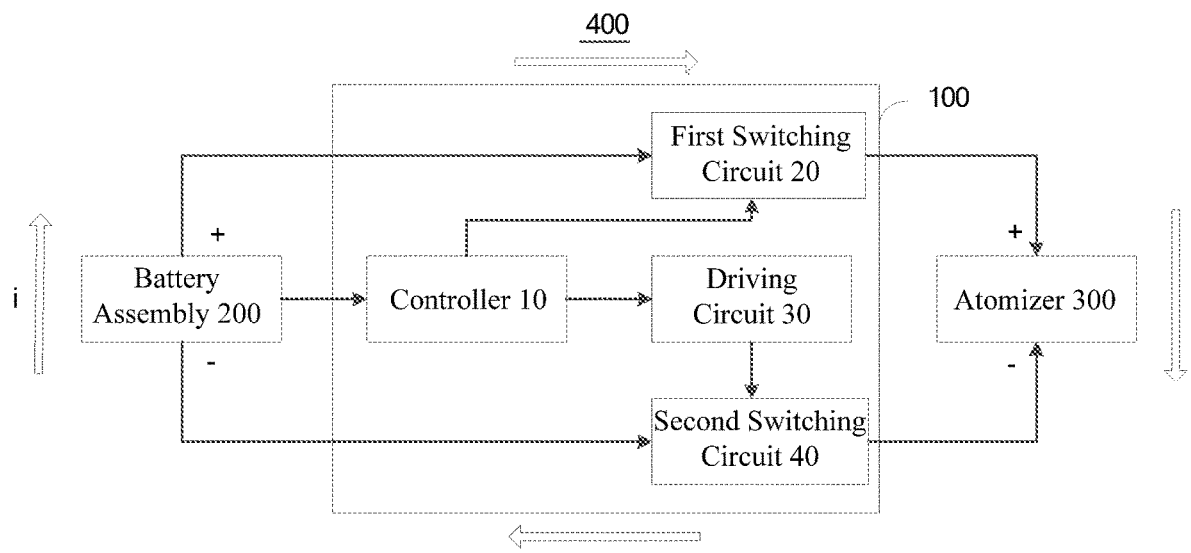
FIG. 1 shows a schematic structural view of an electronic cigarette in accordance with a preferred embodiment of the present invention.

Please refer to FIG. 1, FIG. 1 is schematic structural view of an electronic cigarette in accordance with a preferred embodiment of the present invention. As shown in FIG. 1, an electronic cigarette 400 includes an output control circuit 100, a battery assembly 200 and an atomizer 300. Understandably, the output control circuit 100, the battery assembly 200 and the atomizer 300 are all disposed in an outer shell of the electronic cigarette 400. In particular, the output control circuit 100 is disposed between the battery assembly 200 and the atomizer 300 in order to control power supply connection of the battery assembly 200 with the atomizer 300.

The output control circuit 100 includes a controller 10, a first switching circuit 20, a driving circuit 30 and a second switching circuit 40.

The controller 10 is respectively electrically connected with the battery assembly 200, the first switching circuit 20 and the driving circuit 30. In particular, the controller 10 includes a single-chip microcomputer, a microprocessor or a digital signal processor (DSP). The battery assembly 200 supplies a direct current power to the controller 10, and a voltage value of the direct current power is usually 1.8V (Volt), 3.3V or 5V. When the controller 10 is an integrated circuit, a required voltage for its normal working is available by looking up a data manual of the controller 10.

In a preferred embodiment, the controller 10 is used to control switching-on or switching-off of the first switching circuit 20, and to provide pulse-width modulation (PWM) signals to the driving circuit 30.

The first switching circuit 20 is respectively electrically connected with the battery assembly 200, the controller 10 and the atomizer 300. The first switching circuit 20 works as a switch serially electrically connected between the battery assembly 200 and the atomizer 300. When a smoker starts smoking, the controller 10 controls the first switching circuit 20 to switch on, i.e., switch closed for electrical connection, the battery assembly 200 supplies power to the atomizer 300. The atomizer 300 is then switched on to normally output power. Liquid tobacco in the atomizer 300 is accordingly heated to be atomized. When the smoker quits smoking, the controller 10 controls the first switching circuit 20 to switch off, i.e., switch opened for disconnection, a power supply feeding circuit of the atomizer 300 is cut off. The atomizer 300 stops working, and heating of the liquid tobacco in the atomizer 300 is stopped to terminate atomization of the liquid tobacco.

In particular, the first switching circuit 20, the atomizer 300 and the second switching circuit 40 are electrically connected in series. Understandably, the first switching circuit 20 can be firstly electrically connected with the atomizer 300 in series, and then be electrically connected with the second switching circuit 40 in series. Of course, the first switching circuit 20 can alternatively be firstly electrically connected with the second switching circuit 40 in series, and then be electrically connected with the atomizer 300 in series.

It is required to be explained that, in a preferred embodiment in accordance with the present invention, the first switching circuit 20 is firstly electrically connected with the atomizer 300 in series, and then is electrically connected with the second switching circuit 40 in series. At the moment, the power supply feeding circuit of the atomizer 300 is a circuit formed by starting from a positive electrode of the battery assembly 200, passing the first switching circuit 20, the atomizer 300 and the second switching circuit 40 in sequence, and then returning to a negative electrode of the battery assembly 200. A flowing direction of an electrical current i of the power supply feeding circuit of the atomizer 300 is shown in FIG. 1. If the first switching circuit 20 is firstly electrically connected with the second switching circuit 40 in series and then is electrically connected with the atomizer 300 in series, the power supply feeding circuit of the atomizer 300 is a circuit formed by starting from a positive electrode of the battery assembly 200, passing the first switching circuit 20, the second switching circuit 40 and the atomizer 300 in sequence, and then returning to a negative electrode of the battery assembly 200.

Figure 6:
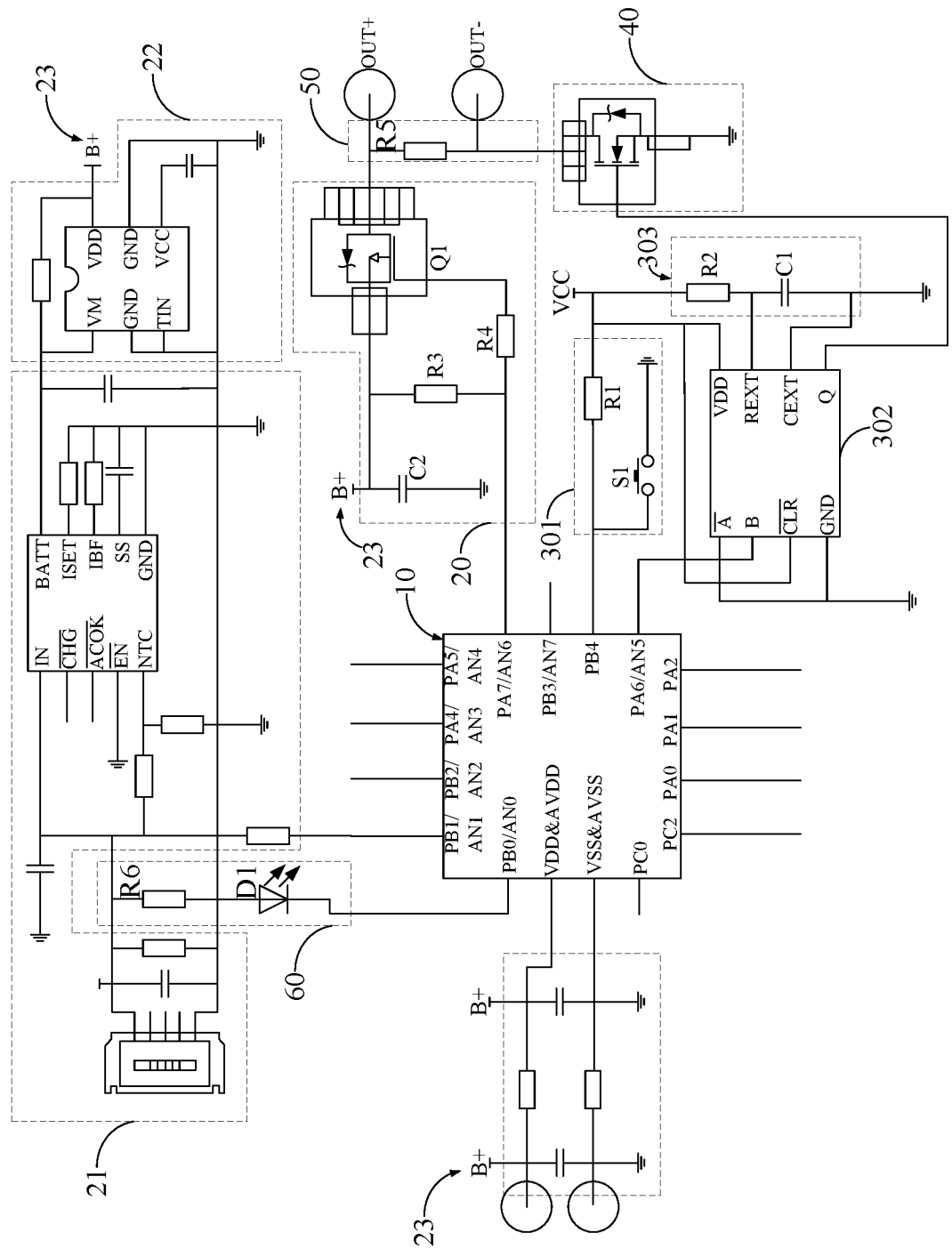
FIG. 6 shows a schematic circuit connection diagram of an output control circuit in accordance with a preferred embodiment of the present invention.

Please refer to FIG. 6 cooperatively. In a preferred embodiment, the first switching circuit 20 includes a second capacitor C2, a third resistor R3, a fourth resistor R4 and a first metal oxide semiconductor field effect transistor (MOSFET, short for "MOS") tube Q1.

In particular, a first end of the second capacitor C2 is electrically connected with the battery assembly 200. A second end of the second capacitor C2 is electrically connected with ground. A first end of the third resistor R3 is respectively electrically connected with the first end of the second capacitor C2 and a source electrode of the first MOS tube Q1. A second end of the third resistor R3 is respectively electrically connected with the controller 10 and a first end of the fourth resistor R4. A second end of the fourth resistor R4 is electrically connected with a gate electrode of the first MOS tube Q1. A drain electrode of the first MOS tube Q1 is electrically connected with a positive electrode of the atomizer 300.

Switching-on or switching-off of the first switching circuit 20 is controlled based on control signals from the controller 10. The first switching circuit 20 can be a switching MOS tube circuit provided as a preferred embodiment of the present invention. Of course, the first switching circuit 20 is not limited to a form of physical circuits provided in the preferred embodiment. For example, the first switching circuit 20 is provided to include only the first MOS tube Q1, or to include a transistor and its peripheral circuits. The first switching circuit 20 can further be other forms of switching circuits, such as relays, contact switches, etc. Switching-on or switching-off of the first switching circuit 20 is controlled based on the control signals from the controller 10. Correspondingly, the control signals include electrical current signals or voltage signals.

Figure 2:
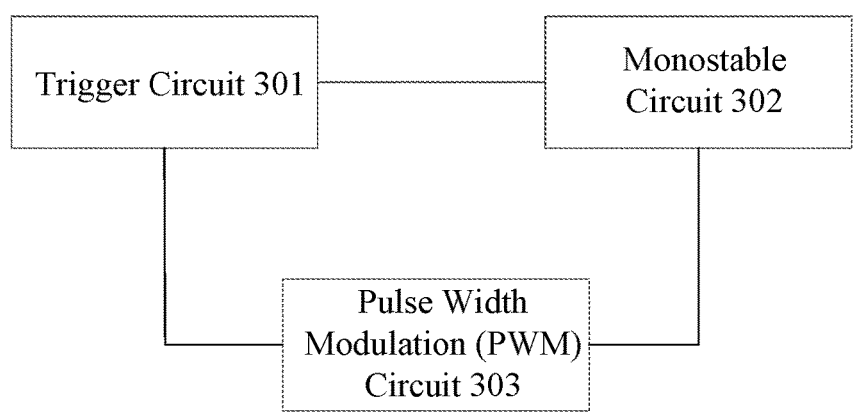
FIG. 2 shows a schematic structural view of a driving circuit in accordance with a preferred embodiment of the present invention.

Please refer to FIG. 2. The driving circuit 30 includes a trigger circuit 301, a monostable circuit 302 and a pulse width modulation (PWM) circuit 303.

In particular, the trigger circuit 301 is respectively electrically connected with the battery assembly 200, the controller 10, the monostable circuit 302 and the PWM circuit 303. The trigger circuit 301 is used for triggering the controller 10 to decide whether or not the monostable circuit 302 is provided with PWM signals.

As shown in FIG. 6, the trigger circuit 301 includes a first resistor R1 and a switch S1. A first end of the first resistor R1 is electrically connected with the controller 10, and a second end of the first resistor R1 is electrically connected with the monostable circuit 302. A first end of the switch S1 is electrically connected with the first end of the first resistor R1, and a second end of the switch S1 is electrically connected with ground.

In particular, the switch S1 is switched on or switched off based on smoke inhaling operation of users. A physical form of the switch S1 can be a mechanical push-button switch or a pneumatic sensor. When the switch S1 is switched on, a sub-circuit of the first resistor R1 is short circuited, voltage at a PB4 port of the controller 10 is 0, and the controller 10 is triggered to provide PWM signals to the monostable circuit 302. When the switch S1 is switched off, voltage at the PB4 port of the controller 10 is a dividing voltage of the first resistor R1 when VCC voltage passes through the first resistor R1, i.e., the voltage at the PB4 port of the controller 10 is at a high voltage level, and the controller 10 is triggered to terminate provision of PWM signals to the monostable circuit 302.

The monostable circuit 302 is further respectively electrically connected with the battery assembly 200, the controller 10, the second switching circuit 40 and the PWM circuit 303. The monostable circuit 302 includes an input and an output. The input is used to receive PWM signals, and the output is used to output high voltage level signals or low voltage level signals in order to control switching on or switching off of the second switching circuit 40 based on the PWM signals.

The monostable circuit 302 is a basic pulse elementary circuit having two working states including a steady state and a transient state. Without externally applied signals (i.e., the PWM signals), the monostable circuit 302 is in the steady state. With triggering of the externally applied signals, the monostable circuit 302 is turned from the steady state to the transient state. After a period of time, the monostable circuit 302 is automatically turned to the steady state. The period of time for being in the transient state is decided based on parameters of the monostable circuit 302 itself, and is irrelevant to a working time of the PWM signals. The monostable circuit 302 can be further used to generate positive/negative pulse signals with a preset time interval, i.e., to output high voltage level signals or low voltage level signals with a preset time interval.

In a preferred embodiment, the monostable circuit 302 includes a 74LVC1G123 integrated circuit chip. In other embodiments, the monostable circuit 302 can be constituted by discrete components and logical gating circuits. Alternatively, the monostable circuit 302 can be realized by using a 555 timer integrated circuit chip (555 timer IC).

The PWM circuit 303 is further electrically connected with the battery assembly 200. The PWM circuit 303 is used to regulate pulse widths of high voltage level signals or low voltage level signals. As shown in FIG. 6, the PWM circuit 303 includes a second resistor R2 and a first capacitor C1. A first end of the second resistor R2 is respectively electrically connected with the battery assembly 200 and the second end of the first resistor R1. A second end of the second resistor R2 is respectively electrically connected with a first end of the first capacitor C1 and the monostable circuit 302. A second end of the first capacitor C1 is electrically connected with ground.

In particular, a ratio between the second resistor R2 and the first capacitor C1 is used to set up pulse widths of output pulses of the monostable circuit 302, i.e., pulse widths of high voltage level signals or low voltage level signals. The PWM circuit 303 adopts a simulative control method, and is able to regulate a base electrode of a transistor or a gate electrode of a MOS tube based on variation of corresponding loads (i.e., pulse widths of high voltage level signals or low voltage level signals) in order to realize change of a turn-on time of the transistor or the MOS tube. As shown in FIG. 6, the monostable circuit 302 is electrically connected with a gate electrode of a second MOS tube Q2. In other embodiments, the PWM circuit 303 adopts, but does not limit to, the performing method published according to the preferred embodiment.

The second switching circuit 40 is respectively electrically connected with the battery assembly 200, the driving circuit 30 and the atomizer 300.

In a preferred embodiment, the second switching circuit 40 includes a second MOS tube Q2. A gate electrode of the second MOS tube Q2 is electrically connected with the output of the monostable circuit 302. A source electrode of the second MOS tube Q2 is electrically connected with ground. A drain electrode of the second MOS tube Q2 is electrically connected with a negative electrode of the atomizer 300. Understandably, in other embodiments, the second switching circuit 40 adopts, but not limit to, the performing method illustrated according to the preferred embodiment.

Figure 3:
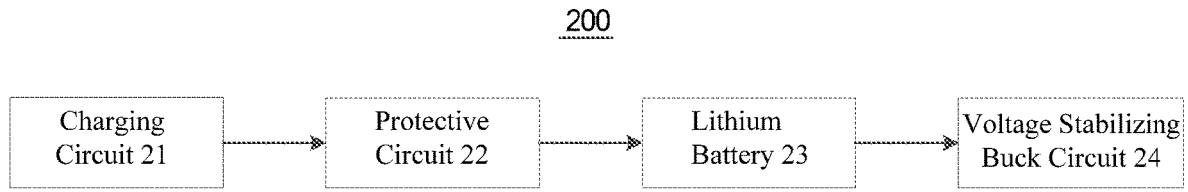
FIG. 3 shows a schematic structural view of a battery assembly in accordance with a preferred embodiment of the present invention.

Please refer to FIG. 3. The battery assembly 200 includes a charging circuit 21, a protective circuit 22, a lithium battery 23 and a voltage stabilizing buck circuit 24. In particular, the protective circuit 22 is electrically connected with the charging circuit 21. The lithium battery 23 and the controller 10 are electrically connected with the driving circuit 30.

In a preferred embodiment, the charging circuit 21 includes a universal serial bus (USB) port circuit, a filter circuit, a power management chip and their peripheral circuits. The protective circuit 22 includes lithium ion/lithium polymer battery protective chip and its peripheral circuits. The protective circuit 22 has functions of voltage and electric current protection against overcharge, voltage and electric current protection against overdischarge, protection against overheating, protection against short circuits, protection against reverse connection of battery cells and protection against reverse connection of chargers, etc.

Since the lithium battery 23 has advantages of high average voltage for a single cell, high energy density, light weight for battery bodies, long lives, strong adaption to high and low temperatures and green environmental protection, etc., in a preferred embodiment, the lithium battery 23 is a priority choice as energy storage equipment for the electronic cigarette 400. The lithium battery 23 is constituted by three parts of battery cells, a protective plate and a plastic shell. The lithium battery 23 is mainly classified as two types, lithium metal batteries and lithium ion batteries. A lithium ion battery does not contain lithium metal, and is chargeable. The lithium ion battery works mainly by movement of lithium ions between a positive electrode and a negative electrode. In a charging/discharging process thereof, lithium ions (Li$^+$) move back and forth between the positive electrode and the negative electrode for intercalation and/or deintercalation. When the lithium ion battery is charged, the lithium ions (Li$^+$) are deintercalated from the positive electrode, and are intercalated into the negative electrode through electrolytes. The negative electrode is in a high lithium concentration state. Discharging of the lithium ion battery is just the other way around.

Understandably, the lithium battery 23 has two processes of a charging process and a discharging process. When the lithium battery 23 is charged, the lithium battery 23 is in an energy storage process. When the lithium battery 23 is discharged, the lithium battery 23 supplies power to the controller 10, the first switching circuit 20 and the driving circuit 30.

In a preferred embodiment, the voltage stabilizing buck circuit 24 is a resistance capacitance step-down circuit. The voltage stabilizing buck circuit 24 is used to lower direct current voltages at two ends of the lithium battery 23 down to a normal working voltage for the controller 10 and the monostable circuit 302.

Figure 4:
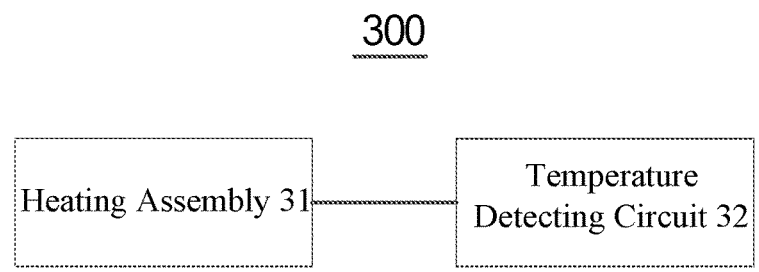
FIG. 4 shows a schematic structural view of an atomizer in accordance with a preferred embodiment of the present invention.

Please refer to FIG. 4. The atomizer 300 includes a heating assembly 31 and a temperature detecting circuit 32 connected with the heating assembly 31. The temperature detecting circuit 32 is electrically connected with the controller 10, and is used to detect temperature values of the heating assembly 31 and to transmit the temperature values to the controller 10.

In other embodiments, the heating assembly 31 includes a wire coil, a coil-winding part and a liquid absorbing part. The liquid absorbing part is contacted with the wire coil in order to conduct absorbed tobacco liquid or tobacco oil toward the wire coil. When the atomizer 300 works normally, the tobacco liquid or tobacco oil is vaporized by the wire coil to generate smoke. If the wire coil has a higher heating quantity, a using life of the wire coil may be caused to be shortened, and the wire coil is therefore required to be replaced. Besides, excess heating may also lead to overheating of an outer shell of the electronic cigarette 400, and may cause shortening a using life of the electronic cigarette 400, etc., and further affect use of the electronic cigarette 400 for its users. Hence, the temperature detecting circuit 32 is added in the electronic cigarette 400 for use of detecting temperature values of the heating assembly 31. When temperature of the heating assembly 31 exceeds a preset temperature threshold, the controller 10 controls to shut down the first switching circuit 20 and/or the second switching circuit 40 in order to further cut off the power supply feeding circuit of the atomizer 300. The heating assembly 31 is then stopped to heat and to avoid extremely high temperature of the heating assembly 31.

As previously mentioned, a physical working process for the electronic cigarette 400 is depicted as follows.

When there is an inhaling action from users, the first switching circuit 20 is controlled to be switched on (i.e., the first MOS tube Q1 is turned on) according to control signals of the controller 10. In the meantime, the trigger circuit 301 triggers the controller 10 to decide whether or not the monostable circuit 302 is provided with PWM signals. The monostable circuit 302 outputs high voltage level signals or low voltage level signals to switch on the second switching circuit 40 (i.e., the second MOS tube Q2 is turned on) based on the PWM signals after the monostable circuit 302 detects the PWM signals. At this moment, the battery assembly 200, the first switching circuit 20, the atomizer 300 and the second switching circuit 40 together form an electric current circuit, i.e., the power supply feeding circuit of the atomizer 300 is electrically connected and the atomizer 300 is switched on.

When the first switching circuit 20 is out of order (i.e., the first MOS tube Q1 stops being turned on), in other words, the above mentioned electric current circuit is disconnected, the atomizer 300 stops working due to no power supply. When the controller 10 is out of order or in a malfunctioned status, the controller 10 stops providing the PWM signals to the monostable circuit 302. The monostable circuit 302 reverses its output high voltage level signals or low voltage level signals when no PWM signals are detected (For example, the gate electrode of the second MOS tube Q2 is set to receive high voltage level signals for turning on the second MOS tube Q2, then the high voltage level signals are reversed to low voltage level signals when the controller 10 is out of order or in the malfunctioned status). The second switching circuit 40, i.e., the above mentioned electric current circuit, is disconnected (i.e., the second MOS tube Q2 stops being turned on). The atomizer 300 stops working due to no power supply.

In conclusion, the first switching circuit 20 and the second switching circuit 40 cannot be switched on simultaneously either when the first switching circuit 20 is out of order or when the controller 10 is out of order or in the malfunctioned status. As a result, a complete electric current circuit between the atomizer 300 and the battery assembly 200 cannot be formed (i.e., the power supply feeding circuit of the atomizer 300 is caused to be disconnected). Safety risk such as fire incidents is avoided when the atomizer 300 of the electronic cigarette 400 continuously outputs power due to the controller 10 being out of order, either one of switching circuits (the first switching circuit 20 or the second switching circuit 40) being out of order, or the controller 10 being in the malfunctioned status. Reliability and safety of products related to the electronic cigarette 400 are therefore enhanced.

Figure 5:
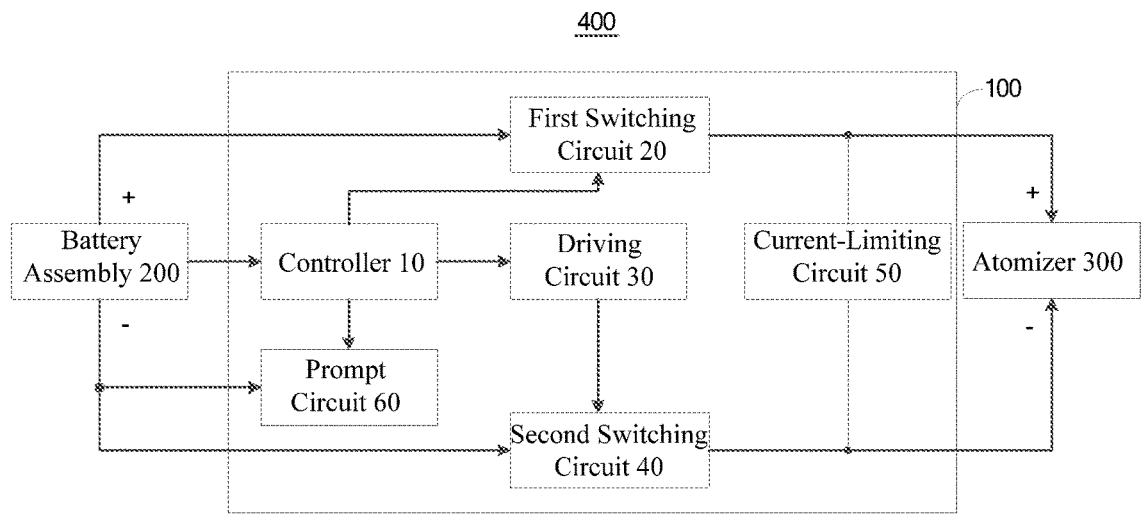
FIG. 5 shows a schematic structural view of an electronic cigarette in accordance with another preferred embodiment of the present invention.

Please refer to FIGS. 5-6. The output control circuit 100 further includes a current-limiting circuit 50 and a prompt circuit 60.

The current-limiting circuit 50 is parallel electrically connected between the positive electrode of the atomizer 300 and the negative electrode of the atomizer 300. The atomizer 300 is electrically connected between a port OUT+ and a port OUT− of the current-limiting circuit 50. The current-limiting circuit 50 includes a fifth resistor R5. The fifth resistor R5 is used for restricting a quantity of electrical currents flowing into the atomizer 300.

The prompt circuit 60 is respectively electrically connected with the charging circuit 21 and the controller 10. The prompt circuit 60 is used to indicate a power output status of the atomizer 300. The power output status includes switching on or switching off of the atomizer 300, and power output ranks of the atomizer 300. In some embodiment, the prompt circuit 60 includes a display for displaying the power output status of the atomizer 300.

In practice, the prompt circuit 60 includes a sixth resistor R6 and a light-emitting diode (LED) tube D1. A first end of the sixth resistor R6 is electrically connected with the charging circuit 21, and a second end of the sixth resistor R6 is electrically connected with a positive electrode of the LED tube D1. A negative electrode of the LED tube D1 is electrically connected with the controller 10.

In some embodiment, a number of the LED tube D1 can be plural. The LED tube D1 can displays at least two kinds of colors. Alternatively, brightness of displayed color of the LED tube D1 can be gradually varied from being bright to dark. For example, the number of the LED tube D1 is 4. When all of the four LED tubes D1 light up, an output power of the atomizer 300 is set to be 20 W, i.e., the atomizer 300 works in a higher power rank. When only one of the four LED tubes D1 counting from a side of the four LED tubes D1 lights up, the output power of the atomizer 300 is set to be 5 W, i.e., the atomizer 300 works in a lower power rank.

The output control circuit 100 is provided in accordance with a preferred embodiment of the present invention. Switching on of the atomizer 300 is simultaneously controlled by the first switching circuit 20 and the second switching circuit 40. Safety risk such as fire incidents is accordingly avoided when the atomizer 300 of the electronic cigarette 400 continuously outputs power due to the controller 10 being out of order, either one of the first and second switching circuits 20, 40 being out of order, or the controller 10 being in the malfunctioned status. Reliability and safety of products related to the electronic cigarette 400 are therefore enhanced.

Finally, it should be noted that the above embodiments are only used to illustrate technical solutions of the present invention, but not to limit them. Under inventive ideas of the present invention, technical features of the above embodiments or different embodiments can also be combined. Steps can be implemented in any order, and there are many other variations in different aspects of the present invention as described above. For the sake of brevity, those variations are not provided in details. Although the present invention has been described in detail with reference to the foregoing embodiments, it should be understood by the ordinary skilled in the art that they can still modify technical solutions recorded in the foregoing embodiments, or equivalently replace some of the technical features. Besides, these modifications or substitutions do not make essence of corresponding technical solutions deviate from the scope of the technical solutions provided in all preferred embodiments of the present invention.

What is claimed is:

1. An output control circuit for an electronic cigarette which comprises a battery assembly and an atomizer, the output control circuit comprising a controller, a first switching circuit, a driving circuit and a second switching circuit, the controller used to control switching-on or switching-off of the first switching circuit, and to provide pulse-width modulation (PWM) signals to the driving circuit;
the first switching circuit respectively electrically connected with the battery assembly, the controller and the atomizer;
the driving circuit electrically connected with the controller, the driving circuit used for driving to switch on or switch off the second switching circuit according to the PWM signals;
the second switching circuit respectively electrically connected with the battery assembly, the driving circuit and the atomizer;
the controller electrically connected with the battery assembly;
wherein the first switching circuit, the atomizer and the second switching circuit are electrically connected in series, the atomizer is switched on when the first switching circuit and the second switching circuit are switched on simultaneously.

2. The output control circuit as claimed in claim 1, wherein the driving circuit comprises a trigger circuit, a monostable circuit and a pulse width modulation (PWM) circuit;
the trigger circuit is respectively electrically connected with the battery assembly, the controller, the monostable circuit and the PWM circuit, the trigger circuit is used for triggering the controller to decide whether or not the monostable circuit is provided with PWM signals;
the monostable circuit is respectively electrically connected with the battery assembly, the controller, the second switching circuit and the PWM circuit, the monostable circuit comprises an input and an output, the input of the monostable circuit is used to receive PWM signals, and the output of the monostable circuit is used to output high voltage level signals or low voltage level signals in order to control switching on or switching off of the second switching circuit based on the received PWM signals;
the PWM circuit is electrically connected with the battery assembly, the PWM circuit is used to regulate pulse widths of the high voltage level signals or low voltage level signals.

3. The output control circuit as claimed in claim 2, wherein the output control circuit further comprises a prompt circuit, the prompt circuit is respectively electrically connected with the charging circuit and the controller;
the prompt circuit comprises a sixth resistor and a light-emitting diode (LED) tube, a first end of the sixth resistor is electrically connected with the charging circuit, and a second end of the sixth resistor is electrically connected with a positive electrode of the LED tube, a negative electrode of the LED tube is electrically connected with the controller.

4. The output control circuit as claimed in claim 2, wherein the trigger circuit comprises a first resistor and a switch;
a first end of the first resistor is electrically connected with the controller, and a second end of the first resistor is electrically connected with the monostable circuit;
a first end of the switch is electrically connected with the first end of the first resistor, and a second end of the switch is electrically connected with ground.

5. The output control circuit as claimed in claim 4, wherein the output control circuit further comprises a prompt circuit, the prompt circuit is respectively electrically connected with the charging circuit and the controller;
the prompt circuit comprises a sixth resistor and a light-emitting diode (LED) tube, a first end of the sixth resistor is electrically connected with the charging circuit, and a second end of the sixth resistor is electrically connected with a positive electrode of the LED tube, a negative electrode of the LED tube is electrically connected with the controller.

6. The output control circuit as claimed in claim 4, wherein the PWM circuit comprises a second resistor and a first capacitor;
a first end of the second resistor is respectively electrically connected with the battery assembly and the second end of the first resistor, a second end of the second resistor is respectively electrically connected with a first end of the first capacitor and the monostable circuit;
a second end of the first capacitor is electrically connected with ground.

7. The output control circuit as claimed in claim 6, wherein the output control circuit further comprises a prompt circuit, the prompt circuit is respectively electrically connected with the charging circuit and the controller;
the prompt circuit comprises a sixth resistor and a light-emitting diode (LED) tube, a first end of the sixth resistor is electrically connected with the charging circuit, and a second end of the sixth resistor is electrically connected with a positive electrode of the LED tube, a negative electrode of the LED tube is electrically connected with the controller.

8. The output control circuit as claimed in claim 1, wherein the first switching circuit comprises a second capacitor, a third resistor, a fourth resistor and a first metal oxide semiconductor field effect transistor (MOS) tube;
a first end of the second capacitor is electrically connected with the battery assembly, a second end of the second capacitor is electrically connected with ground;
a first end of the third resistor is respectively electrically connected with the first end of the second capacitor and a source electrode of the first MOS tube, a second end of the third resistor is respectively electrically connected with the controller and a first end of the fourth resistor;
a second end of the fourth resistor is electrically connected with a gate electrode of the first MOS tube;
a drain electrode of the first MOS tube is electrically connected with a positive electrode of the atomizer.

9. The output control circuit as claimed in claim 8, wherein the output control circuit further comprises a prompt circuit, the prompt circuit is respectively electrically connected with the charging circuit and the controller;
the prompt circuit comprises a sixth resistor and a light-emitting diode (LED) tube, a first end of the sixth resistor is electrically connected with the charging circuit, and a second end of the sixth resistor is electrically connected with a positive electrode of the LED tube, a negative electrode of the LED tube is electrically connected with the controller.

10. The output control circuit as claimed in claim 8, wherein the second switching circuit comprises a second MOS tube, a gate electrode of the second MOS tube is electrically connected with an output of a monostable circuit of the driving circuit, a source electrode of the second MOS tube is electrically connected with ground, a drain electrode of the second MOS tube is electrically connected with a negative electrode of the atomizer.

11. The output control circuit as claimed in claim 10, wherein the output control circuit further comprises a prompt circuit, the prompt circuit is respectively electrically connected with the charging circuit and the controller;

the prompt circuit comprises a sixth resistor and a light-emitting diode (LED) tube, a first end of the sixth resistor is electrically connected with the charging circuit, and a second end of the sixth resistor is electrically connected with a positive electrode of the LED tube, a negative electrode of the LED tube is electrically connected with the controller.

12. The output control circuit as claimed in claim 10, wherein the output control circuit further comprises a current-limiting circuit, the current-limiting circuit is parallel electrically connected between the positive electrode of the atomizer and the negative electrode of the atomizer;

the current-limiting circuit comprises a fifth resistor, the fifth resistor is used for restricting a quantity of electrical currents flowing into the atomizer.

13. The output control circuit as claimed in claim 12, wherein the output control circuit further comprises a prompt circuit, the prompt circuit is respectively electrically connected with the charging circuit and the controller;

the prompt circuit comprises a sixth resistor and a light-emitting diode (LED) tube, a first end of the sixth resistor is electrically connected with the charging circuit, and a second end of the sixth resistor is electrically connected with a positive electrode of the LED tube, a negative electrode of the LED tube is electrically connected with the controller.

14. The output control circuit as claimed in claim 12, wherein the battery assembly comprises:

a charging circuit;

a protective circuit, the protective circuit being electrically connected with the charging circuit;

a lithium battery, the lithium battery being electrically connected with the protective circuit;

a voltage stabilizing buck circuit, the voltage stabilizing buck circuit being respectively electrically connected with the lithium battery, the controller and the driving circuit.

15. The output control circuit as claimed in claim 14, wherein the output control circuit further comprises a prompt circuit, the prompt circuit is respectively electrically connected with the charging circuit and the controller;

the prompt circuit comprises a sixth resistor and a light-emitting diode (LED) tube, a first end of the sixth resistor is electrically connected with the charging circuit, and a second end of the sixth resistor is electrically connected with a positive electrode of the LED tube, a negative electrode of the LED tube is electrically connected with the controller.

16. The output control circuit as claimed in, claim 1, wherein the output control circuit further comprises a prompt circuit, the prompt circuit is respectively electrically connected with the charging circuit and the controller;

the prompt circuit comprises a sixth resistor and a light-emitting diode (LED) tube, a first end of the sixth resistor is electrically connected with the charging circuit, and a second end of the sixth resistor is electrically connected with a positive electrode of the LED tube, a negative electrode of the LED tube is electrically connected with the controller.

17. The output control circuit as claimed in claim 1, wherein the atomizer comprises a heating assembly and a temperature detecting circuit connected with the heating assembly, the temperature detecting circuit is electrically connected with the controller, and is used to detect temperature values of the heating assembly and to transmit the temperature values to the controller.

* * * * *